US008608792B2

(12) United States Patent
Silveira et al.

(10) Patent No.: US 8,608,792 B2
(45) Date of Patent: Dec. 17, 2013

(54) ENDOPROSTHESIS AND DELIVERY SYSTEM FOR DELIVERING THE ENDOPROSTHESIS WITHIN A VESSEL OF A PATIENT

(75) Inventors: Pierre G. Silveira, Florianopolis-SC (BR); Luana Beatriz Pértile Dezanet, Goias (BR); Luciano Almeida Fleury Curado, Goias (BR); Thiago Semão Pires, Goias (BR); Douglas José da Silva, Goias (BR); Eduardo Jose Cordeiro, University Heights, OH (US)

(73) Assignee: Scitech Produtos Medicos LTDA, Goias (BR)

( * ) Notice: Subject to any disclaimer, the term of this patent is extended or adjusted under 35 U.S.C. 154(b) by 44 days.

(21) Appl. No.: 13/069,184

(22) Filed: Mar. 22, 2011

(65) Prior Publication Data
US 2011/0224774 A1 Sep. 15, 2011

Related U.S. Application Data

(63) Continuation-in-part of application No. 12/198,742, filed on Aug. 26, 2008, now abandoned.

(60) Provisional application No. 61/316,153, filed on Mar. 22, 2010.

(30) Foreign Application Priority Data

Nov. 30, 2007 (BR) .................................. PI 0704464

(51) Int. Cl.
*A61F 2/06* (2013.01)

(52) U.S. Cl.
USPC ........................................ 623/1.11; 623/1.35

(58) Field of Classification Search
USPC ............. 623/1.11, 1.13, 1.15, 1.16, 1.2, 1.23, 623/1.35; 606/108, 191, 194, 198, 200
See application file for complete search history.

(56) References Cited

U.S. PATENT DOCUMENTS 5,562,724 A    10/1996  Vorwerk et al.
6,051,020 A *   4/2000  Goicoechea et al. ........ 623/1.35
(Continued)

FOREIGN PATENT DOCUMENTS

WO    WO 9633066 A1    10/1996
WO    WO 01/67993         9/2001
(Continued)

*Primary Examiner* — Ryan Severson
*Assistant Examiner* — Katherine M Shi
(74) *Attorney, Agent, or Firm* — Tarolli, Sundheim, Covell & Tummino LLP

(57) ABSTRACT

An endoprosthesis is disclosed for implantation at a bifurcation between a main vessel and at least two secondary vessels. The endoprosthesis includes first and second bodies. Each body includes a self-expanding and flexible structure having a proximal region, an intermediate region, and a distal region. The distal region terminates at a free end. The flexible structure defines a leg and a support member adjacent to the leg. The leg terminates at the free end of the distal region. The second body is positioned within the first body. The proximal region of the first body includes a free end configured for positioning within the main vessel. The leg of the first body is configured for positioning within a first secondary vessel. The leg of the second body is configured for positioning within a second secondary vessel.

14 Claims, 11 Drawing Sheets

(56) References Cited

U.S. PATENT DOCUMENTS

| | | |
|---|---|---|
| 6,149,682 A | 11/2000 | Frid |
| 6,287,329 B1 * | 9/2001 | Duerig et al. ............ 623/1.11 |
| 6,379,372 B1 | 4/2002 | Dehdashtian et al. |
| 6,673,102 B1 | 1/2004 | Vonesh et al. |
| 6,802,859 B1 | 10/2004 | Pazienza et al. |
| 6,872,224 B1 | 3/2005 | Telxelra Moretra et al. |
| 6,942,691 B1 | 9/2005 | Chuter |
| 7,112,217 B1 | 9/2006 | Kugler |
| 2001/0037142 A1 | 11/2001 | Stelter et al. |
| 2001/0039450 A1 | 11/2001 | Pavcnik et al. |
| 2003/0120338 A1 | 6/2003 | Chobotov et al. |
| 2003/0176911 A1 | 9/2003 | Iancea et al. |
| 2003/0208256 A1 * | 11/2003 | DiMatteo et al. ......... 623/1.11 |
| 2003/0220681 A1 | 11/2003 | Chobotov et al. |
| 2004/0098079 A1 * | 5/2004 | Hartley et al. ............ 623/1.11 |
| 2005/0049676 A1 * | 3/2005 | Nazzaro et al. ........... 623/1.13 |
| 2005/0096737 A1 | 5/2005 | Shannon et al. |
| 2005/0113906 A9 * | 5/2005 | Bolduc et al. ............. 623/1.35 |
| 2006/0025850 A1 | 2/2006 | Frederick et al. |
| 2006/0036314 A1 | 2/2006 | Perez et al. |
| 2006/0085012 A1 | 4/2006 | Dolan |
| 2006/0142836 A1 | 6/2006 | Hartley et al. |
| 2006/0173533 A1 | 8/2006 | Chobotov |
| 2006/0184229 A1 | 8/2006 | Elliott |
| 2006/0224227 A1 | 10/2006 | Chobotov |
| 2006/0276872 A1 | 12/2006 | Arbefeuille et al. |
| 2007/0027531 A1 | 2/2007 | DiMatteo et al. |
| 2007/0118145 A1 * | 5/2007 | Fischer et al. ............... 606/99 |
| 2009/0143850 A1 | 6/2009 | Silveira |
| 2010/0049313 A1 * | 2/2010 | Alon et al. ................ 623/2.11 |

FOREIGN PATENT DOCUMENTS

| | | |
|---|---|---|
| WO | WO 02/15951 | 2/2002 |
| WO | WO 02051336 A1 | 7/2002 |
| WO | WO 2004/105637 | 12/2004 |
| WO | WO 2005/025456 | 3/2005 |
| WO | WO 2005/039442 | 5/2005 |

\* cited by examiner

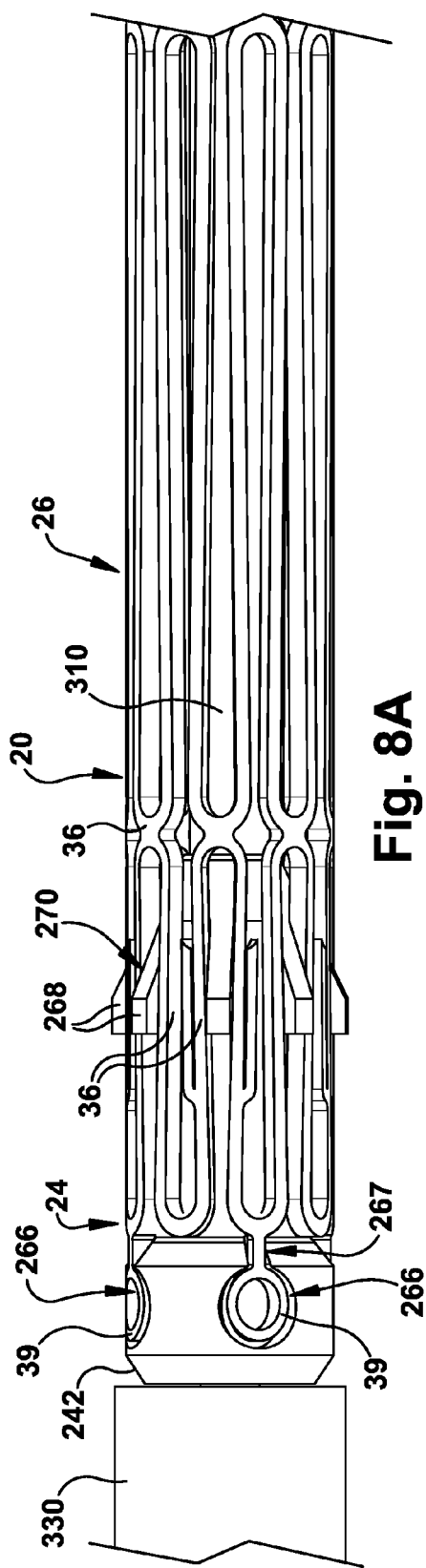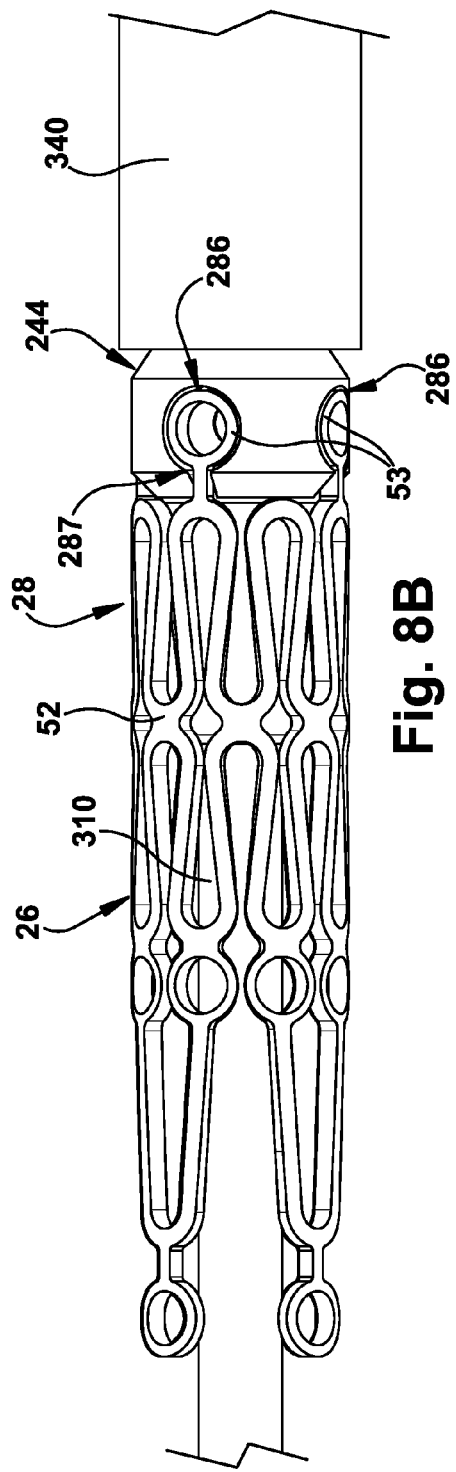

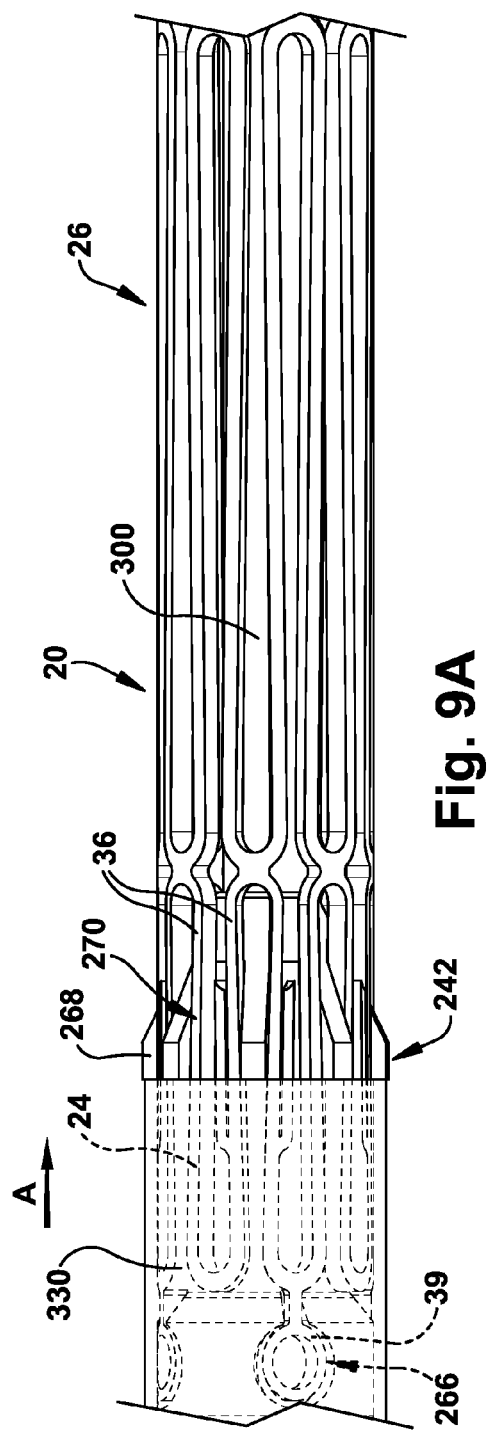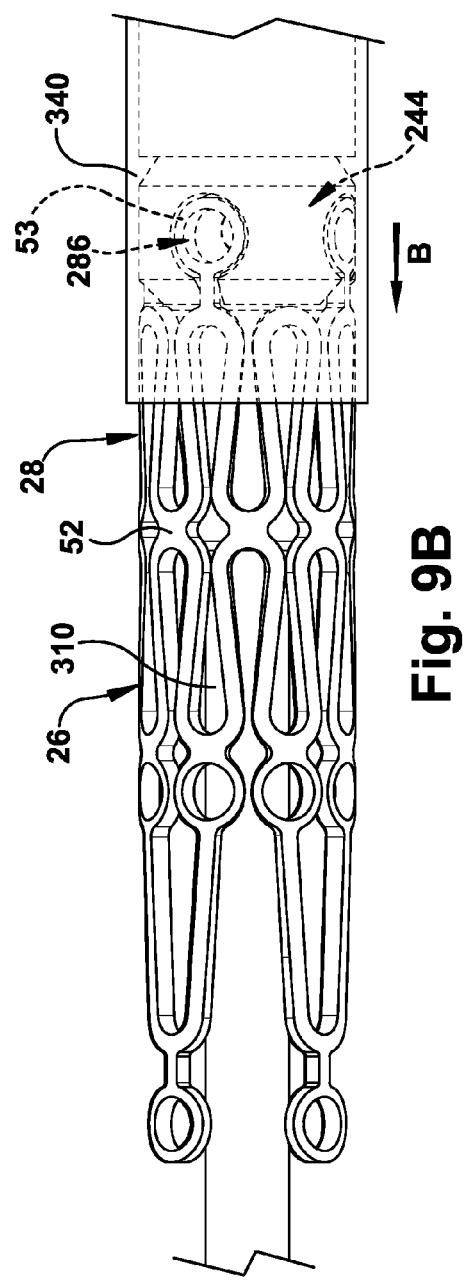

ENDOPROSTHESIS AND DELIVERY SYSTEM FOR DELIVERING THE ENDOPROSTHESIS WITHIN A VESSEL OF A PATIENT

CROSS-REFERENCES TO RELATED APPLICATIONS

This application claims the benefit of U.S. provisional Patent Appln. No. 61/316,153, filed Mar. 22, 2010, and is a continuation-in-part of U.S. patent application Ser. No. 12/198,742, filed Aug. 26, 2008 now abandoned, which claims priority to Brazilian Patent Appln. No. PI 0704464-0, filed in Brazil on Nov. 30, 2007. Each of the above-identified applications is expressly incorporated herein by reference in their entirety.

TECHNICAL FIELD

The invention relates to an endoprosthesis and delivery system for delivering the endoprosthesis within a vessel of a patient.

BACKGROUND

An aneurysm of the abdominal aorta is a dilatation of the walls of this vessel in the abdominal region. The aorta is the bodies' main artery, ascending from the heart's left ventricle to arch around and descend through the thorax and abdomen to finally divide into the two common iliac arteries that supply blood to the pelvis and lower limbs. Aneurysms usually occur in the abdominal part of the aorta below the kidneys. Failure to treat this condition may eventually result in the rupture of the dilatation (aneurysm) causing a massive hemorrhage in a very short period of time with fatal consequences. This is the reasons that treatments such as implanting a reinforcing prosthesis inside the dilated part of the aorta walls are vital to save patients lives. Despite abdominal aortic aneurysms being the most common, they are not restricted to the abdominal area. Aneurysms may also occur, for example, in the aorta thoracica.

The disruptions caused by of the abdominal aortic aneurysms are very serious and may lead to death. Until recently, treatment of aortic aneurysms consisted of invasive surgery methods for inserting a graft inside the aorta to reinforce the artery. Such a procedure requires a surgical incision to allow access to the vessel, which may result in rupture of the aneurysm due to the sudden reduction in the external pressure exerted by the neighboring organs and tissues which are displaced during access procedure. Quite apart from this serious issue, other risk factors include loss of blood and consequent weakness, aneurysm and low blood pressure associated to the abdominal aortic aneurysm. As a result of the inherent risks and complexity of surgical procedures, several alternative devices and methods have been proposed for implanting a graft inside vessels for the treatment of aneurysms.

However, despite the advances represented by the use of stent and stent-graft devices, they have revealed failings both with regard their implanting processes and performance. As described in U.S. Patent Publication No. US2006/184229, these failings may be classified into four main categories. Type I failings are related to the occurrence of leakage between the vascular endoprosthesis and the vessel walls in the area of the proximal aorta immediately above the aneurysm and, therefore, results in continued blood flow to the aneurismal sac, which thus maintains the pressure at this point and favors continued expansion and consequent rupture of the aneurysm. Type I failings may also be caused by the irregular shape of the vessel and/or calcified topography of the aorta lumen which results in poorly inserted circular prostheses in non-circular lumens of the aorta. Type II failings are related to blood flowing through collateral vessels in the dilated area of the aneurysm which requires a further embolization procedure. Type III failings are of mechanical origin and result from excessive wear of the metal/non-metal interface or the poor integrity of a connection or connections between the modular components of a prosthesis. Lastly, the type IV failings are related to excessive porosity of the prosthesis walls which allows the blood to migrate through the walls despite the soundness of all mechanical seals and connections. To remedy usual Type I failings, US2006/184229 proposes an implantable prosthesis with a radially expandable tubular body with at least one flap extending through it.

U.S. Pat. No. 5,562,724 describes an endovascular graft prosthesis to be positioned in—or close to—a bifurcation of the arterial system of a patient, with this prosthesis comprising a main tubular body having a bag-shape and provided with two outlet openings wherein the said main body is intended for location in the principal upstream artery above the bifurcation and having tubular legs joining the main body and adapted to extend into the two downstream arteries. The positioning of the main body in relation to the radially expansive stent devices and the entire assembly in the arteries is done through the use of guide wires. Although such a device does represent an advance compared to former techniques involving surgical procedures, it still presents failings related to its unfavorable displacement along the blood flow and the precision required when correctly positioning the device at the time of implant. The device described in U.S. Patent Publication No. US2007/027531 also uses a system of guide wires to facilitate the implant operation of the device, which comprises at least one filamentous tubular member having a distal extremity and a proximal extremity with a hollow nucleus to receive the guide wire that helps position the device at the intended location.

U.S. Pat. No. 6,802,859 proposes a bifurcated graft implant having a trunk portion and a portion with independent flexible legs wherein the entire assembly (main portion plus legs) may constitute a unitary body or be formed of modular elements. To ensure the flexibility of the bifurcation, this graft is supported by a stent lattice throughout. Despite this device being self-expanding and having appropriate flexibility at the region of bifurcation, it remains difficult to implant at the intended location.

Another device for the repair of abdominal aortic aneurysms is proposed in U.S. Pat. No. 6,942,691. This device comprises a modular graft that includes two elements configured to be inserted into each other over an extension sufficiently long as to form a resistant seal yet remaining flexible enough to adapt to the region of the bifurcation. The said device comprises a first and second modular element with each expanding from an originally compressed state so as to allow implantation at the intended aneurysm location. The graft described in U.S. Pat. No. 6,942,691 is practical since it allows insertion of both component elements at an intended location but, nevertheless, it presents inconveniences related to the stability of its placement and the relative safety of the large blood flow expected through it.

A solution to facilitate the implant of a device in the region of an aneurysm of the abdominal aorta is proposed in document U.S. Patent Publication No. US2003/120338. This solution relates to providing means to allow the use of a catheter having a very small diameter in the delivery systems for devices within the bodies of patients. The proposed device includes a graft having proximal and distal extremities and is provided with a connector member arranged or fixed at one or both extremities, having one or more connector elements wherein the said connector member may be enclosed within multiple layers of the graft body section. Despite this solution being of interest due to the use of a reduced diameter catheter, this device described in US2003/120338 is complex and presents the disadvantage of being difficult to position correctly at its intended location. A similar device also presenting the same disadvantage is described in document U.S. Patent Publication No. US2006/173533 (corresponding to European Patent No. EP1464301).

To correct the issues of stent graft instability, unwanted displacement from the required position and material fatigue, document WIPO Patent Publication No. WO 2001/67993 proposes a stent graft assembly comprising a main body having an ipsilateral leg and a contralateral stump that, combined, form a bifurcation at the distal extremity. A delivery system for this stent graft assembly is also proposed.

WIPO Patent Publication No. WO 2006/014952 (corresponding to U.S. Patent Publication No. US2006/025850) describes an endoprosthesis comprising (i) a main body having a tubular structure configured to attach firmly to a vessel and serve as a seal preventing blood from reaching the aneurysm, (ii) a section constituted of two legs allowing the passage of fluids to the main body and having multiple stent elements and, (iii) a graft attached to the main body and the two legs. This type of endoprosthesis presents the disadvantage of greater implanting difficulty since it consists of a unitary body insufficiently flexible to adjust well at its intended position.

Another fundamental aspect for the treatment of aneurysms using endoprostheses relates to the methods of implanting these and appropriate means for this delicate operation.

Several delivery systems have been proposed aiming to ensure these features. For example, document U.S. Pat. No. 6,379,372 (corresponding to Brazilian Patent No. PI 9712034) describes a delivery and implant system for use inside a body lumen, e.g., a blood vessel, for a radially expandable endoluminal prosthesis with the said system comprising: (a) a delivery catheter, (b) an introducer assembly, and (c) a dilator. Despite this system allowing the safe introduction of an expandable endoluminal prosthesis, it presents major limitations, such as those relating to providing the means for performing the expansion of the prosthesis in an aneurysm in the vicinity of a bifurcation, i.e., an abdominal aortic aneurysm, as well as preventing the control of fine adjustments required to any of the endoprosthesis components once implanted at the intended location. The delivery devices described in documents U.S. Pat. No. 6,673,102 (corresponding to Canadian Patent No. CA 2503480) and U.S. Pat. No. 6,872,224 (corresponding to Brazilian Patent No. PI 9900959) allow greater flexibility for adjusting the different portions of the endoprostheses at their place of implant and use small diameter catheters but, nevertheless, present the same limitations as the system described in document U.S. Pat. No. 6,379,372.

U.S. Pat. No. 7,112,217 describes a delivery system and method for an endoprosthesis that allows adjustment of the various parts at the place of implant. However, this system and method presents the disadvantage that the link between the main body and the legs of the endoprosthesis is based on the coupling of stents fitted to the extremities of these parts and, furthermore, requires an incision of the artery to introduce the endoprosthesis implanting catheter.

U.S. Patent Publication No. US2001/037142 reveals a delivery system and method for endovascular devices comprising: (i) a first sheath with distal and proximal extremities and at least a first expandable device at the proximal extremity, (ii) a second movable sheath inside the first sheath having respective distal and proximal extremities and containing a second expandable device and (iii) trigger buttons linked to the first and second expandable devices. Despite this system allowing the implant of an endoprosthesis and the adjustment of the various component parts, it neither provides the means of fine adjusting nor correcting the position of the endoprosthesis during the implant operation. The endoprosthesis delivery systems described in WIPO Patent Publication No. WO 01566504 (corresponding to U.S. Patent Publication Nos. US2006/224227 and US 2003/220681) also present the same limitations.

U.S. Patent Publication No. US2006/036314 describes a delivery system for endoprostheses that allows implanting the device in a bifurcated vessel but, however, this system does not allow any means of fine adjusting or correcting the position of the endoprosthesis during the implant operation.

U.S Patent Publication No. US2006/085012 illustrates a procedure for implanting an endoprosthesis using a delivery system without, however, describing implanting in a bifurcated vessel which is an operation requiring further steps for expanding the different parts of the endoprosthesis, such as, for example, the main body and the legs extending into the arteries branching from the trunk vessel in which the main body of the endoprosthesis is located. The delivery system described in document U.S. Patent Publication No. US2006/142836 also presents similar failings. However, the delivery system described in U.S. Patent Publication No. US2006/276872 (corresponding to PI 0414109) is intended for implanting this type of device in a curved vessel, i.e., the arched part of the aorta, where guide wire type delivery systems such as those described in documents WIPO Patent Publication Nos. WO 02051336 and WO 2005/039442 cannot be used. Despite the system described in US2006/276872 being appropriate for curved sections of vessels such as the aorta, it does not meet the requirements for implanting endoprostheses in the vicinity of bifurcations and neither provides a means for correcting the position of the endoprosthesis during the implant process.

Although the endoprostheses and implanting systems mentioned above represent significant advances, mainly since they replace surgical techniques, it remains necessary to improve these devices as well as the methods for implanting them and applying them to varying biological conditions.

SUMMARY OF THE INVENTION

The invention relates to an endoprosthesis and delivery system for delivering the endoprosthesis within a vessel of a patient.

According to one example embodiment, an endoprosthesis for implantation at a bifurcation between a main vessel and at least two secondary vessels includes first and second bodies. Each body includes a self-expanding and flexible structure having a proximal region, an intermediate region, and a distal region, the distal region terminating at a free end. The flexible structure of each body defines a leg and a support member adjacent to the leg, the leg terminating at the free end of the distal region. The second body is positioned within the first body. The proximal region of the first body includes a free end configured for positioning within the main vessel. The leg of the first body is configured for positioning within a first secondary vessel. The leg of the second body is configured for positioning within a second secondary vessel.

In another example embodiment, a method of treating the vessel of a patient includes providing first and second bodies, each including a self-expanding and flexible structure. The flexible structure of each body includes a proximal region, an intermediate region, and a distal region, the distal region terminating at a free end. The flexible structure of each body defines a leg and a support member adjacent to the leg, the leg terminating at the free end of the distal region. A free end of the proximal region of the first body is positioned within the main vessel and the free end of the distal region of the first body is positioned within the first secondary vessel. The second body is inserted into the first body such that the proximal region of the second body is positioned within the proximal region of the first body, the leg of the second body extends through the support member of the first body and the support portion of the first body extends into the leg of the second body. The free end of the distal region of the second body is positioned within a second secondary vessel.

In accordance with another example embodiment, an endoprosthesis for implantation at a bifurcation between a main vessel and at least two secondary vessels includes a first body having a lining and a self-expanding and flexible structure connected to the lining. The flexible structure includes a proximal region, an intermediate region, and a distal region. The proximal region terminates at a free end that is free of the lining The intermediate region is attached to the lining The distal region terminates at a free end that is free of the lining The flexible structure defines a leg and a support portion adjacent to the leg. The leg terminates at the free end of the distal region. A second body includes a lining and a self-expanding and flexible structure connected to the lining. The flexible structure includes a proximal region, an intermediate region, and a distal region. The proximal region and the intermediate region are attached to the lining. The distal region terminates at a free end that is free of the lining. The flexible structure defines a leg and a support member adjacent to the leg. The leg terminates at the free end of the distal region. The second body is positioned within the first body such that the proximal region of the second body is positioned with the proximal region of the first body. The leg of the second body extends through the support member of the first body and the support portion of the second body extends into the leg of the first body.

BRIEF DESCRIPTION OF THE DRAWINGS

FIG. 8A illustrates the distal support member of FIG. 6 having a portion of the first body of FIG. 1 crimped thereon.

FIG. 8B illustrates the proximal support member of FIG. 7 having another portion of the first body of FIG. 1 crimped thereon.

FIG. 9A illustrates the distal support member of FIG. 6 in which a portion of the first body crimped thereon is covered by a sleeve.

FIG. 9B illustrates the proximal support member of FIG. 7 in which a portion of the first body crimped thereon is covered by a sleeve.

DETAILED DESCRIPTION

Figure 1:
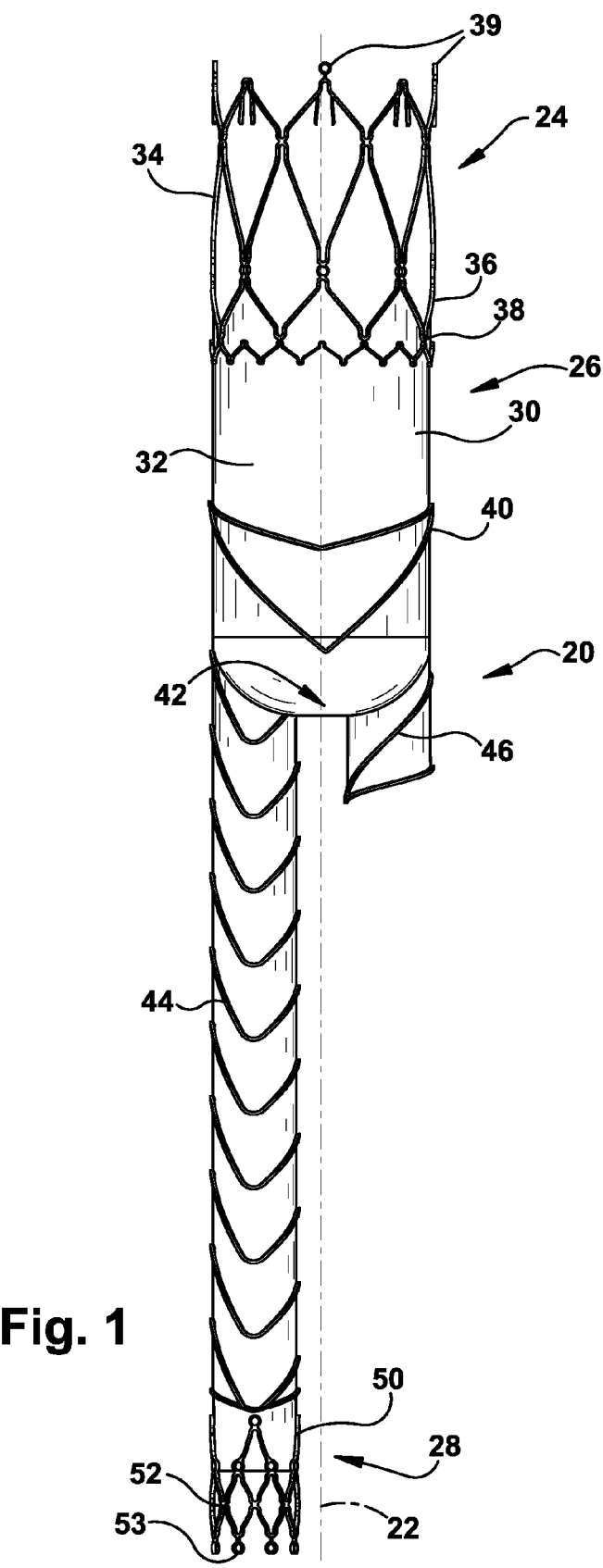
FIG. 1 illustrates a first body of an endoprosthesis according to an example embodiment.

An endoprosthesis implemented according to the invention is intended for the treatment of anomalies of the vessels conveying biological fluids, e.g., blood, in humans. For instance, the endoprosthesis 10 can be percutaneous, which reduces or eliminates the surgical procedure normally necessary in cases of vessel deformation, such as, for example, blood vessels. The percutaneous endoprosthesis 10 may be used in the treatment of aneurysms, such as aneurysms occurring in the vicinity of bifurcations of a main vessel, e.g., aortic aneurysms or abdominal aortic aneurysms. The fact that the endoprosthesis 10 is percutaneous allows it to be implanted in the patient by mere puncture without the need to dissect any vessels, e.g., the iliac arteries, while providing sufficient access for the delivery system to position and release the endoprosthesis.

The endoprosthesis 10 includes a first body 20 and a second body 70. Each body 20, 70 is composed of a stable yet flexible structure, e.g., a metal structure, formed by a series of self-expanding stents that define an elongated sidewall of the flexible structure. For instance, the flexible structure can be formed of one wire that is formed over a mandrel in a continuous helical or spiral shape dimensioned and configured for insertion in a vessel as described herein. A graft or lining 30 may be secured to portions of the first body 20. Alternatively, the lining 30 may be omitted from the first body 20. The materials used for the lining 30 may be natural, artificial or synthetic fibrous materials or a combination or natural and synthetic materials, coated or not. The lining described in documents WIPO Patent Publication No. WO 2002/15951, Brazilian Patent No. PI 9608191 (corresponding to WIPO Patent Publication No. WO 9633066 and U.S. Patent Publication No. US2005/096737) and WIPO Patent Publication No. WO 2005/025456 (corresponding to Canadian Patent No. CA 2539110) may be cited as examples. Alternatively, the lining 30 material may be made of polyester (polyethylene terephthalate) or expanded polytetrafluorethylene (PTFE).

The first and second bodies 20, 70 each extend along a longitudinal central axis 22 and 72, respectively, and are divided into three regions, namely; a proximal region 24, 74, an intermediate region 26, 76, and a distal region 28, 78. The terms "proximal" and "distal" as used herein are intended to mean the portion closer to the heart and the portion furthest from the heart, respectively. It will be understood, however, that the orientation of the bodies 20, 70 could be reversed depending on the configuration of the vessel in which the endoprosthesis 10 is implanted.

The proximal region 24 of the first body 20 includes a stent without a lining at its upper extremity or free end (referred to herein as either free end or free stent) 34. In other words, the free end 34 of the proximal region 24 is lining free, but is still secured to the lining 30. As an example, the free end 34 may be stitched to the lining 30 in an abutting manner at two or more points. The use of a limited number of sutures, e.g., about two, connecting the free end 34 to the lining 30 contributes to reducing the transverse or cross-section of the endoprosthesis 10 material. The free end 34 may be made of metal. For example, the free end 34 may be made of a nickel-titanium alloy such as nitinol or other similar material. The free end 34 serves the main purpose of fixing the first body 20 and, thus, the endoprosthesis 10 to the walls of a vessel such as the aorta.

As can be seen in FIG. 1, the free end 34 has a meshed configuration in which a series of individual wires 36 are secured to one another to form the mesh. Alternatively, a nitinol tube may be laser cut such that the remaining material forms a flexible, wired meshed configuration (not shown). It will be understood that the free end 34 could be formed entirely of individual wires 36, entirely of a laser cut nitinol tube or from a combination thereof.

In the case that the free end 34 is formed of several laser cut or individual wires 36 or, alternatively, of a wire having superposed regions, the wires may be fitted with appropriate forms of attachment, such as springs or some other means of attachment by conformation, to one another. The wires 36 may be fitted with additional means of attachment, such as barbs or hooks (not shown), which help fix the free end 34 to the artery walls by their engagement with and/or insertion into the artery walls. The shape of the free end 34 provides the endoprosthesis 10 with good resistance to possible displacement induced by the flow of biological fluids, e.g., blood, in the vessel. It should also be noted that endoprosthesis migration is a frequent and recurrent problem occurring with the devices presently available on the market.

With the intent of perfecting the attachment and adjustment of the endoprosthesis 10 to the artery shape, the proximal region 24 of the first body 20 can also be fitted with two or more wires 36 stitched to the lining 30 to form one or more rings 38 that conform to the configuration of the artery, when implanted, such that the endoprosthesis can occupy the entire perimeter of the artery. That is, these rings 38 act to seal the proximal region 24 with the arterial wall, and thereby prevent blood flow from inside the endoprosthesis 10 to the artery walls.

The proximal region 24 of the first body 20 further includes one or more attachment members 39 that extend from the wires 36 of the free end 34 for releasably securing the first body to a delivery system for delivering the proximal region of the first body to a predetermined vascular site within the patient. The attachment members 39 may include loops extending generally axially from the free end 34 of the first body 20.

The intermediate region 26 of the first body 20 presents a structure that can be formed of a single shaped wire 40. This wire 40 has the purpose of maintaining the lining 30 open and thereby facilitating unobstructed blood flow through the vessel. Optionally, this structure 40 may also be reduced to a minimum leaving the contralateral second body 70 to keep the endoprosthesis 10 open.

As shown in the example of FIG. 1, the intermediate region 26 of the first body 20 contains a bifurcation 42 in which an elongated leg 44 and a support member 46 are positioned on opposite sides of the central axis 22. The leg 44 is longer than the support member 46. For instance, the leg can be dimensioned and configured to be positioned within one of the main artery branches, such as the iliac artery at the time of implant. The metal structure of the leg 44 may be helical in shape and may be made of the same material (e.g., nickel-titanium alloy) that is used in the intermediate region 26 of the first body 20.

The support member 46 has the purpose of serving as a seal between the first body 20 and the second body 70. For instance, the support member 46 is received in a portion of the second body 70 to provide a seal between the first body 20 and the second body. The support member 46 may include a single wire or multiple wires or other types of flexible support structures configured in any suitable pattern for providing a seal between the first body 20 and the second body 70 when the bodies are connected together (see, e.g., FIG. 3).

The proximal region 24 and intermediate region 26 of the first body 20 may not be continuous with one another. For example, the wires 36, 40 may not be directly connected to one another but instead can be connected solely by the lining 30. In this instance, a part of the first body 20 does not have the metal structure, thereby allowing for better adjustment of the endoprosthesis 10 in tortuous arteries. Alternatively, the wires 36, 40 of the proximal region 24 and the intermediate region 26 can be interconnected such that the proximal region and the intermediate region are continuous with one another (not shown).

FIG. 1 shows that similar to the proximal region 24, the distal region 28 of the first body 20 also includes an end 52 that is free of lining 30 material but is still attached to the lining material. The free end 52 includes a stent that is connected to the distal end thereof. The stent at the free end 52 is dimensioned and configured for fixing the distal extremity of the endoprosthesis 10 to the walls of the secondary vessel. The free end or stent 52 can be configured similar to the free end or stent 34 as disclosed herein. For instance, the free stent 52 can include one or more wires 50 in the shape of a suspended saddle stitched to the lining 30 at only two points. As with the stent 34, the wires 50 of the free stent 52 may be a series of individual wires 36 secured to one another. Alternatively, a nitinol tube may be laser cut such that the remaining material forms the suspended saddle shape configuration of the free stent 52 (not shown). It will be understood that the free end 52 could be formed entirely of individual wires 50, entirely of a laser cut nitinol tube or from a combination thereof.

Optionally, the free stent 52 may be fitted with additional means of attachment, such as barbs or hooks (not shown) that help fix the endoprosthesis 10 to the secondary vessel wall. In any case, the free end 52 further includes one or more attachment members 53 for releasably securing the distal region 28 of the first body 20 to the delivery system for delivering the distal region of the first body to the predetermined vascular site within the patient. The attachment members 53 may include loops extending generally axially from the free end 52 of the distal region 28 of the first body 20.

Figure 2A:
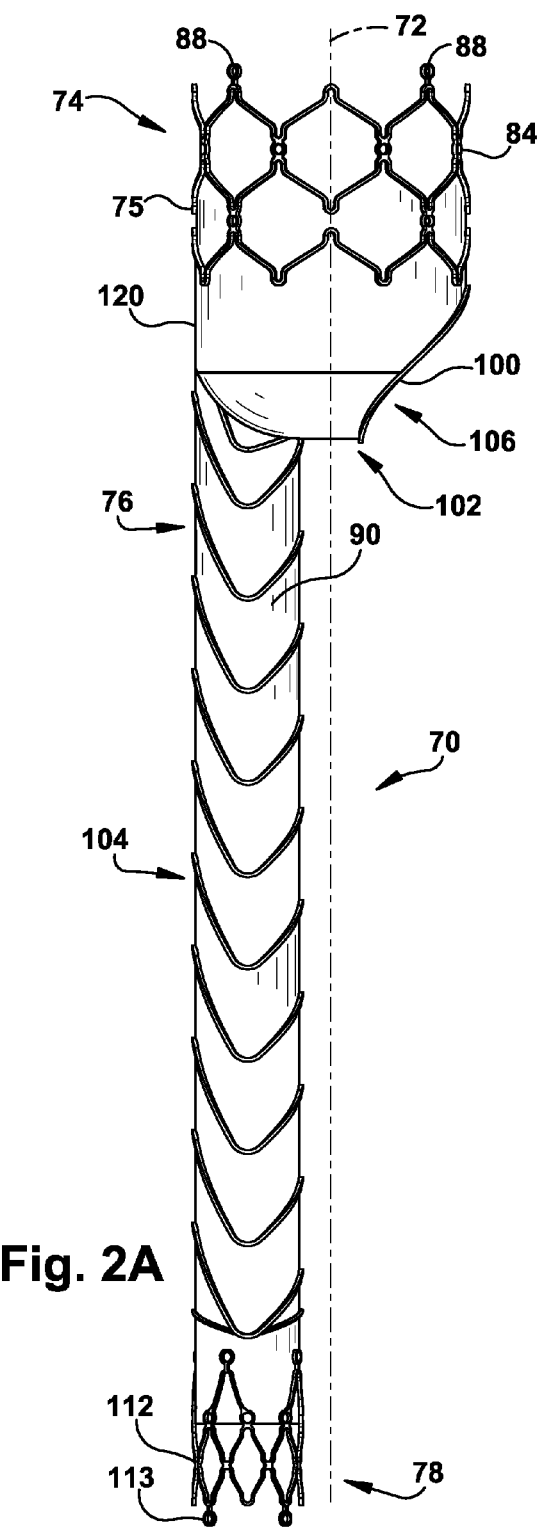
FIG. 2 illustrates a second body of the endoprosthesis according to an example embodiment.
Figure 2B:
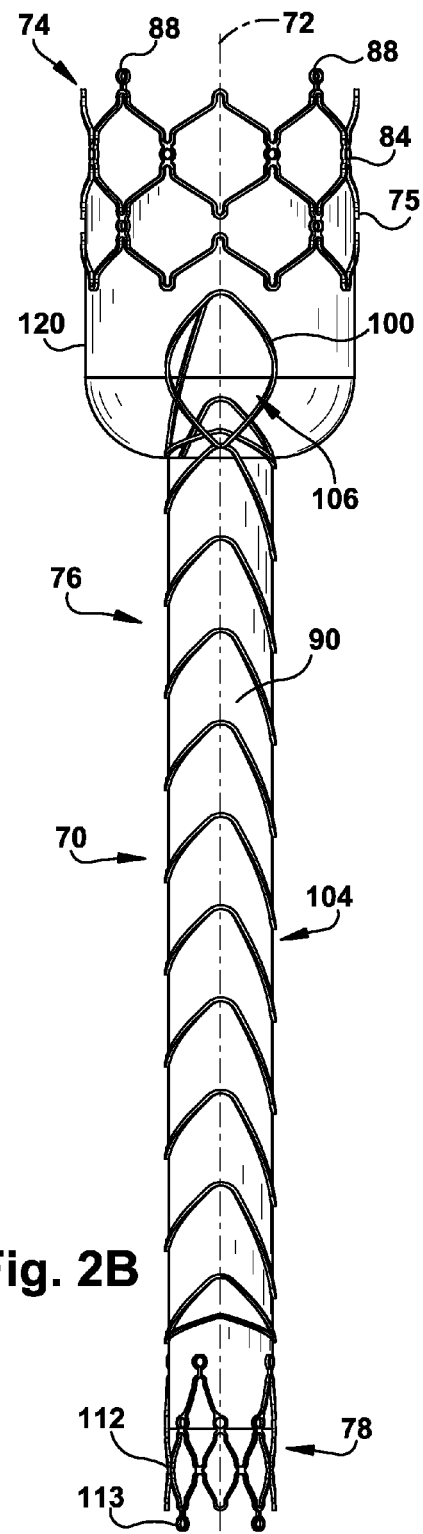

FIG. 2 shows the second body 70 of the endoprosthesis 10 according to an example embodiment. As with the first body 20, the second body 70 may be provided with a graft or lining 90 similar to the lining 30. Alternatively, the lining 90 may be omitted from the second body 70 (not shown). The second body 70 can be shorter than the first body 20 but also has a helical structure throughout its entire available transverse or cross-section that maintains the lining 90 open when used. The second body 70 can be formed of a metal, such as a nickel-titanium alloy.

As one example, the proximal region 74 of the second body 70 may be provided with a free end or stent 75 that may be similar to the free stent 34 of the first body 20 or, alternatively, may be a conventional Z-stent, i.e., a Z-shaped wire. The free stent 75 of the proximal region 74 of the second body 70 is formed by one or more wires 84 and may be designed to occupy a portion of the first body 20 not having a metal structure or with minimal metal structure, thereby increasing the rigidity and stability of the first body and, thus, the rigidity of the endoprosthesis 10 when assembled. The free stent 75 has a meshed configuration in which a series of individual wires 84 are secured to one another to form the mesh. Alternatively, a nitinol tube may be laser cut such that the remaining material forms the flexible, wired meshed configuration (not shown). It will be understood that the free stent 75 could be formed entirely of individual wires 84, entirely of a laser cut nitinol tube or from a combination thereof.

The proximal region 74 further includes at least one attachment member 88 that extends from the wires 84 of the free end 75 for attaching the proximal region of the second body 70 to the proximal region 24 of the first body 20. As shown in FIG. 2, the attachment member 88 may include one or more looped structures that cooperate with correspondingly configured structure (not shown) on the first body 20 in order to receive fasteners or sutures for securing the second body 70 to and within the first body. The attachment members 88 may also act to help secure the proximal region 74 of the second body 70 to the delivery system for placing the second body within the first body 20 inside the vascular site as will be described.

The intermediate region 76 of the second body 70 is provided with a bifurcation 102 from which a contra-lateral leg 104 with respect to the leg 44 of the first body 20 extends. The leg 104 is dimensioned and configured to be positioned inside another secondary branch of the main vessel, e.g., the iliac artery, when implanting the endoprosthesis 10. A support member 106 allowing blood flow is located to one side of the contra-lateral leg 104 on the opposite side of the central axis 72. The support member 106 may include a single wire or a plurality of wires arranged in a predetermined configuration.

The proximal region 74 and the intermediate region 76 of the second body 70 are connected by a reinforcing member 120 that includes at least one wire arranged in a predetermined pattern. For example, the reinforcing member 120 may have a helical shape and may include one or more coils between the proximal region 74 and the intermediate region 76 of the second body 70.

The distal region 78 of the second body 70 where the leg 104 terminates is provided with a free stent or end 112 that may be similar to the free stent 52 of the leg 44 of the first body 20 or may alternatively be a Z-stent. In other words, the free end 112 of the leg 104 is not lined with the lining 90 but may be secured thereto in an abutting manner at a predetermined number of points, e.g., two or more points. The free end 112 has a meshed configuration in a series of individual wires are secured to one another to form the mesh. Alternatively, a nitinol tube may be laser cut such that the remaining material forms a flexible, wired meshed configuration (not shown). It will be understood that the free end 112 could be formed entirely of individual wires, entirely of a laser cut nitinol tube or from a combination thereof.

The free end 112 of the second body 70 further includes one or more attachment members 113 for releasably securing the distal region 78 of the second body 70 to the delivery system for delivering the second body to the predetermined vascular site within the patient. The attachment members 113 may include loops extending generally axially from the free end 112 of the distal region 78 of the second body 70.

Figure 3:
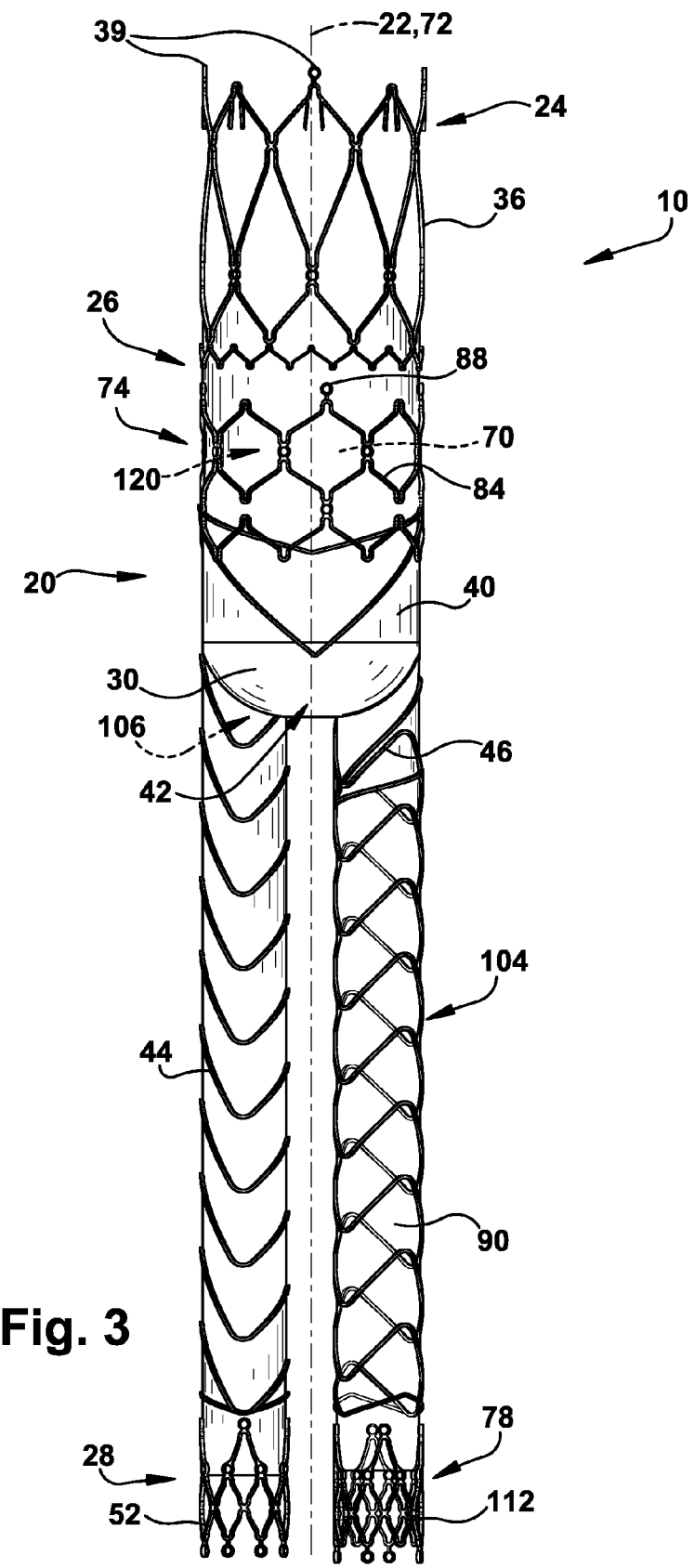
FIG. 3 is an illustration of the second body inserted into the first body to form the endoprosthesis according to an example embodiment.

FIG. 3 shows the endoprosthesis 10 according to an example embodiment entirely assembled, which is accomplished by inserting the second body 70 into the first body 20 such that the central axis 22 of the first body is aligned with the central axis 72 of the second body. The endoprosthesis 10 is configured such that the first body 20 and the second body 70 are complementary with one another and form a substantially perfect bifurcation when assembled that substantially resists becoming disconnected. The walls of the assembled endoprosthesis 10 are formed from a double layer of the lining 30 and the lining 90. This dual lining configuration therefore provides twice the protection against the effects of the repeated secondary demands imposed by the pulsing of biological fluids through the endoprosthesis 10.

When the endoprosthesis 10 is assembled the proximal region 74 of the second body 70 is positioned within the proximal region 24 of the first body 20. Therefore, the attachment members 88 on the proximal region 74 of the second body 70 are aligned with portions of the proximal region 24 of the first body 20. This configuration allows fasteners such as sutures to secure the second body 70 to the first body 20 and thereby stabilize the endoprosthesis 10. Additionally, the support member 106 of the second body 70 is aligned with the leg 44 of the first body 20 and the elongated leg 104 of the second body 70 can be inserted into and pass through the corresponding leg of the first body. Accordingly, the support member 106 of the second body 70 provides inner support and guidance for the leg 44 of the first body 20. Likewise, the support member 46 of the first body 20 provides outer support and guidance for the leg 104 of the second body 70. Furthermore, the superposition of the support member 46 of the first body 20 and the leg 104 of the second body 70 as well as the support member 106 of the second body and the leg 44 of the first body form seals between both bodies and prevents blood leakage.

Inserting the second body 70 into the first body 20 also positions the reinforcing member 120 of the second body between the proximal region 24 and the intermediate region 26 of the first body. The reinforcing member 120 helps to reinforce this portion of the first body 20 while still allowing relative movement between the proximal regions 24, 74 and intermediate regions 26, 76 of the first and second bodies 20, 70. This relative movement provides greater flexibility for the endoprosthesis 10 to accommodate more tortuous vessels within the patient. If the first body 20 is provided with a lining 30 and the proximal region 24 of the first body 20 is not continuous with the intermediate region 26, the reinforcing member 120 helps to reinforce the unsupported lining 32.

The assembled, bifurcated endoprosthesis 10 allows free blood flow to both branches of the trunk vessel, e.g., the two iliac arteries. Currently available devices on the market are based on the concept of two superimposed endoprostheses, i.e., a bifurcated main body and a contra-lateral extension. On the other hand, the configuration of the endoprosthesis 10 according to the present invention confers to the device good stability and further can eliminate contra-lateral leg disconnection.

The division of the endoprosthesis 10 structure into two bodies 20, 70 constitutes a further advantage over conventional endoprostheses because the material area is divided and, thus, it is possible to implant both bodies separately using small caliber catheters, e.g., a 14F catheter. Furthermore, the endoprosthesis 10 according to the present invention may be provided with sensory means (not shown) for measuring and monitoring the patient's condition and position, such as, for example, the sensor device described in document WIPO Patent Publication No WO 2004/105637.

Another aspect of the invention relates to a delivery system 200 for delivering the endoprosthesis 10 in a piece-wise manner to the intended place of implant within a vessel conveying biological fluids in a patient.

Figure 4:
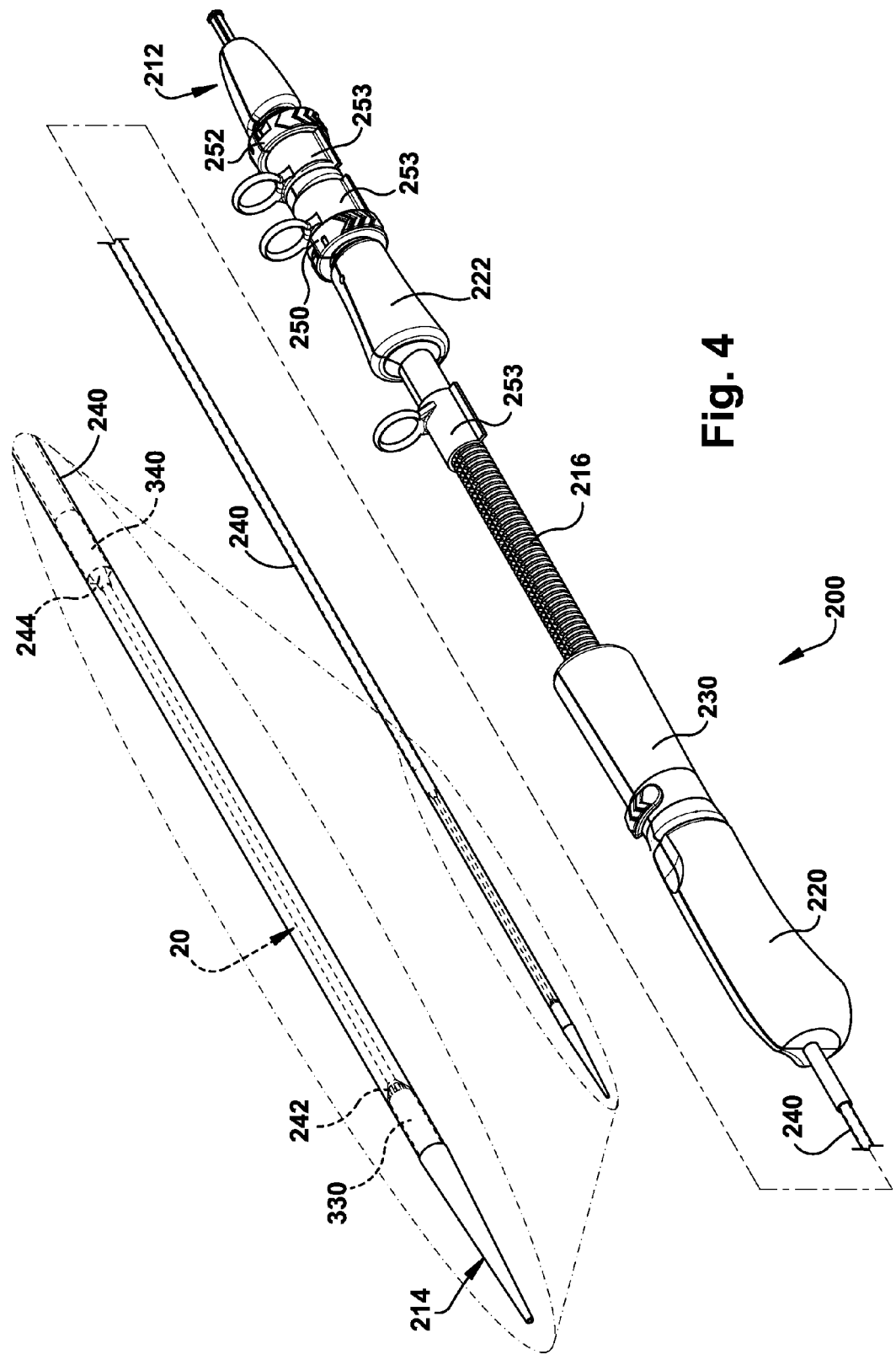
FIG. 4 illustrates a representation of the delivery system according an embodiment of the invention.
Figure 5:
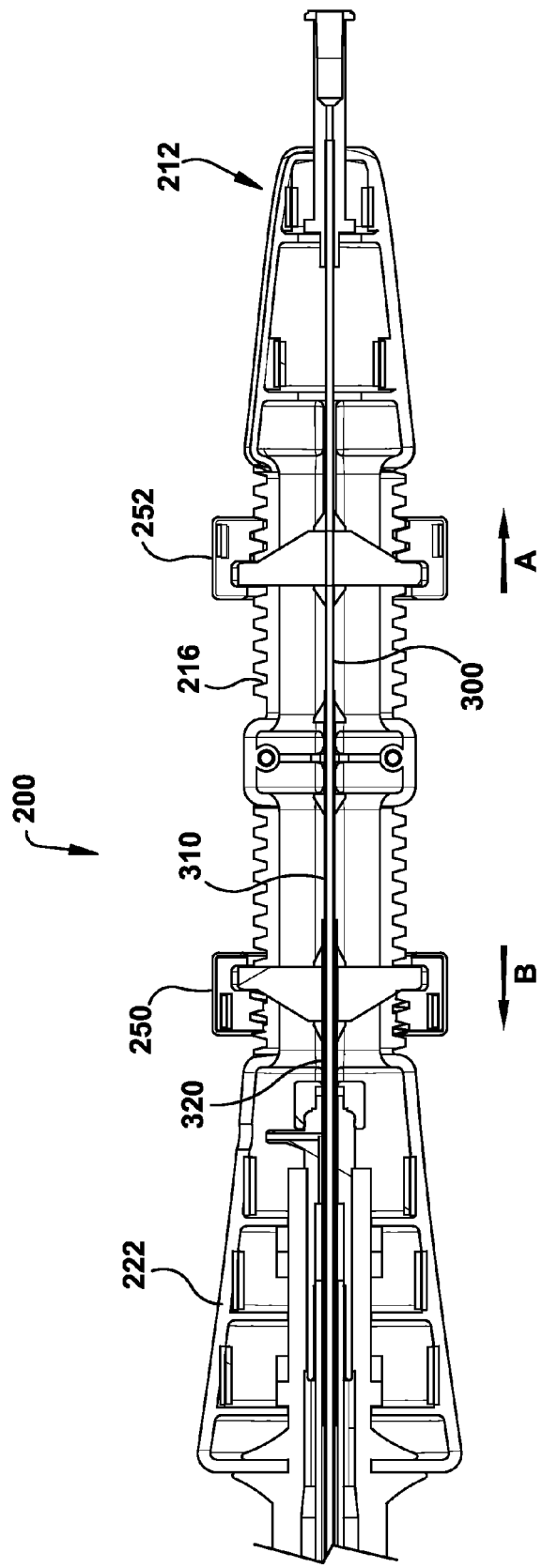
FIG. 5 illustrates a sectional view of a portion of the delivery system of FIG. 4.

FIGS. 4-5 show an example of the delivery system 200 that can be utilized for implanting each of the first and second bodies 20, 70 separately and sequentially to assemble the endoprosthesis 10 within the vascular site. The delivery system 200 comprises a catheter that includes a proximal end 212 and a distal end 214. A threaded base rod 216 is positioned at the proximal end 212 and threadably receives portions of the delivery system 200 to assist in delivering the endoprosthesis 10 to the vessel. A front handle 220 and a rear handle 222 are fixed to the threaded rod 216 at the proximal end 212 of the delivery system 200 to aid in manipulating the delivery system.

The delivery system 200 acts as an attachment device for the endoprosthesis 10. For example, the free end 34 of the proximal region 24 of the first body 20 and the free end 52 of the distal region 28 of the first body are releasably secured to the delivery system 200. Attaching both ends 34, 52 of the first body 20 to the delivery system 200 allows the surgeon to maintain complete control of the position of the first body when implanting the first body within the vascular site.

Before or during implantation of the first body 20 into the vessel, the free end 75 of the proximal region 74 of the second body 70 and the free end 112 of the distal region 78 of the second body are secured to a second, identical delivery system 200 and subsequently released from the second delivery system within the first body 20 to fully assemble the endoprosthesis 10 within the vascular site. Therefore, the bodies 20, 70 of the endoprosthesis 10 are loaded onto and released from separate and substantially similar delivery systems 200 in accordance with the present invention.

The delivery system 200 includes the following mechanisms for conveying, positioning, fine adjustment, and delivering the first and second bodies 20, 70 of the endoprosthesis 10 to the desired vessel according to the present invention: (a) locking mechanism 230, (b) outer sleeve 240 and inner sleeves 330, 340, (c) distal and proximal support members 242, 244 for releasably holding the bodies of the endoprosthesis, and (d) first and second trigger mechanisms 250, 252. A series of concentric tubes 300, 310, 320 (FIG. 5) interconnects the trigger mechanisms 250, 252, sleeves 330, 340, and support members 242, 244.

The following detailed discussion of the delivery system 200 describes the use of the delivery system with the first body 20 of the endoprosthesis 10. It will be understood, however, that the delivery system 200 operates in the same manner with the second body 70 following implantation of the first body into the vessel. For instance, after implantation of the first body 20 into the vessel, the second body 70 is positioned within the first body, and released from the delivery system to form the endoprosthesis 10 within the vessel.

A cross-section of the delivery system 200 is illustrated in FIG. 5. In FIG. 5, each of the tubes 300, 310, 320 extends through the threaded rod 216 from the proximal end 212 of the delivery system 200 towards the distal end 214 (not shown). The tubes 300, 310, 320 are hollow and concentric. The tube 300 is secured to the second trigger mechanism 252 and mechanically connects the second trigger mechanism to the inner sleeve 330 (see FIG. 4). The tube 310 extends over the tube 300 and is fixed to the threaded rod 216 and to both the distal support member 242 and the proximal support member 244 (see FIG. 4). The tube 320 extends over the tube 310, is secured to the first trigger mechanism 250, and mechanically connects the first trigger mechanism to the inner sleeve 340 (see FIG. 4). The tube 300 and the tube 320 are capable of independently sliding axially relative to one another and relative to the tube 310 and threaded rod 216. Due to this configuration, axial movement of the first and second trigger mechanisms 250, 252 results in axial movement of the inner sleeve 340 and the inner sleeve 330, respectively.

Figure 6:
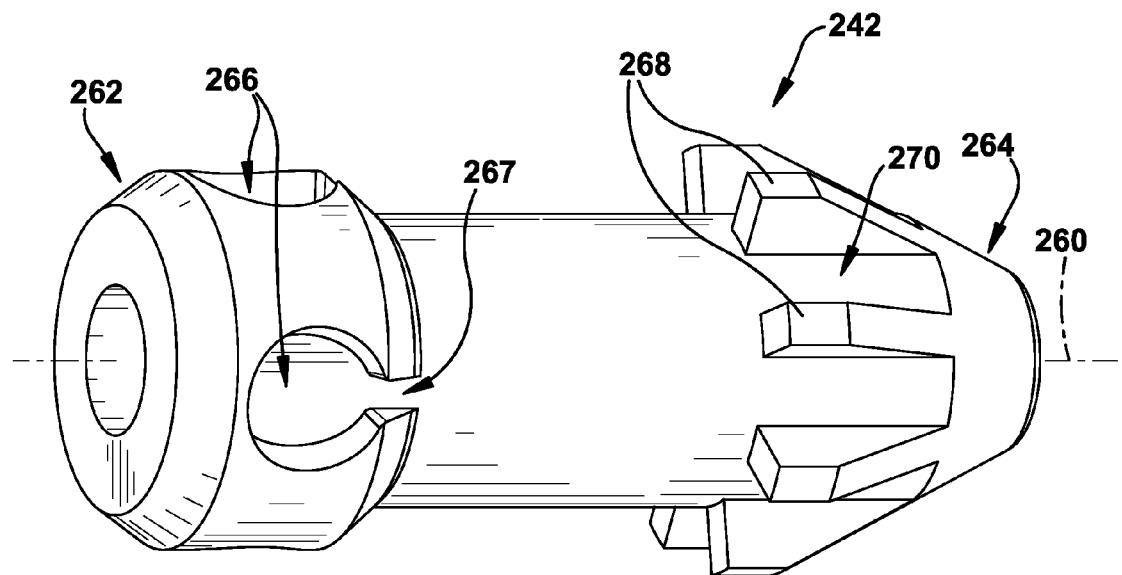
FIG. 6 illustrates a distal support member of the delivery system of FIG. 4.
Figure 7:
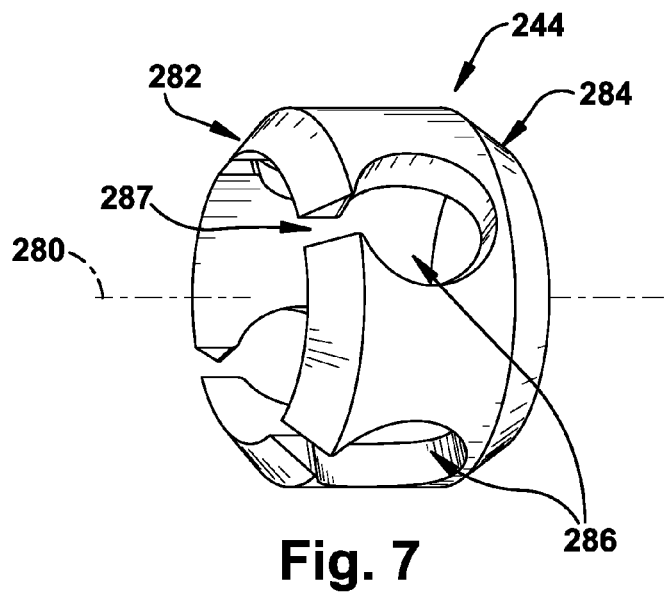
FIG. 7 illustrates a proximal support member of the delivery system of FIG. 4.

The distal support member 242 and proximal support member 244 that releasably hold the first body 20 of the endoprosthesis 10 are illustrated in FIGS. 6-7. The distal support member 242 has a generally cylindrical shape and extends along an axis 260 between a distal end 262 positioned nearer the distal end 214 of the delivery system 200 and a proximal end 264 positioned nearer the proximal end 212 of the delivery system. The distal support member 242 is generally co-axial with the threaded rod 216, tubes 300, 310, 320, and sleeves 240, 330, 340 of the delivery system 200. The distal support member 242 includes a series of blind openings 266 radially spaced around the axis 260. The blind openings 266 are sized and positioned about the distal support member 242 for receiving the attachment members 39 in the free end 34 of the proximal region 24 of the first body 20. Each opening 266 extends to a corresponding axially extending passage 267 for receiving a portion of the wires 36 extending from each attachment member to the remainder of the free end 34 of the proximal region 24 of the first body 20.

The distal support member 242 further includes a series of axially extending projections or fingers 268 that are spaced radially about the distal support member. The projections 268 extend radially outwardly from a surface of the distal support member to define axially extending passages 270 (between each adjacent pair of projections). At least some of the passages 270 can be aligned with the passages 267 and are sized and configured to receive the wires 36 of the free end 34 of the first body 20 when the first body is in a collapsed condition in order to help retain the collapsed first body on the distal support member 242.

As shown in FIG. 7, the proximal support member 244 is configured similar to the distal support member 242 except that the proximal support member does not have axially extending projections. The proximal support member 244 has a generally cylindrical shape and extends along an axis 280 between a distal end 282 positioned nearer the distal end 214 of the delivery system 200 and a proximal end 284 positioned nearer the proximal end 212 of the delivery system. The proximal support member 244 is generally co-axial with the threaded rod 216, tubes 300, 310, 320, and sleeves 240, 330, 340. The proximal support member 244 includes a series of blind openings 286 radially spaced around the axis 280 of the distal support member. The blind openings 286 are sized and positioned about the proximal support member 244 for receiving the attachment members 53 in the distal region 28 of the first body 20. Each opening 286 extends to a corresponding axially extending passage 287 for receiving the wires connecting each attachment member 53 to the remainder of the free end 52 of the distal region 28 of the first body 20.

To load the first body 20 onto the delivery system 200, the first body is collapsed and the proximal region 24 is crimped onto the distal support member 242 in the manner described and shown in FIG. 8A. For example, each attachment member 39 on the proximal region 24 of the first body 20 is positioned within an associated opening 266 on the distal support member 242 and the wires 36 extending from each attachment member are positioned within the corresponding passages 267 and within the passages 270 between the projections 268. In this configuration, the intermediate region 26 of the first body 20 overlies and abuts the tube 310 extending between and secured to the distal and proximal support members 242, 244. When the proximal region 24 of the first body 20 is crimped to the distal support member 242, the proximal region of the first body assumes a compacted cross-section that is smaller than the cross-section of the inner sleeve 330.

The distal region 28 of the first body 20 is then crimped onto the proximal support member 244 as shown in FIG. 8B such that each attachment members 53 on the distal region are positioned within the openings 286 on the proximal support member and the wires of the free end 52 extending from each attachment member are positioned within the passages 287 between the projections 286. When the distal region 28 of the first body 20 is crimped to the proximal support member 244, the distal region of the first body assumes a compacted cross-section that is smaller than the cross-section of the inner sleeve 340.

As shown in FIG. 8A, the inner sleeve 330 is positioned distal to the distal support member 242 and is movable to selectively cover the openings 266 of the distal support member in order to retain the proximal region 24 of the first body 20 on the distal support member. For example, the sleeve 330 associated with the distal support member 242 is connected to the tube 300 (see FIG. 5) and therefore is connected to the second trigger mechanism 252 threaded to the threaded rod 216. Axial movement of the second trigger mechanism 252 thereby causes axial movement of the tube 300 and, thus, axial movement of the sleeve 330 relative to the distal support member. Therefore, the second trigger mechanism 252 may be operated to axially move the sleeve 330 to selectively cover and uncover the proximal region 24 of the first body 20 of the endoprosthesis 10.

Likewise, as shown in FIG. 8B, the inner sleeve 340 is positioned proximal to the proximal support member 244 and is movable to selectively cover the openings 286 of the proximal support member in order to retain the distal region 28 of the first body 20 on the proximal support member. For example, the sleeve 340 associated with the proximal support member 244 is connected to the tube 320 (see FIG. 5) and therefore is connected to the first trigger mechanism 250. Axial movement of the first trigger mechanism 250 thereby causes axial movement of the tube 320 and, thus, axial movement of the sleeve 340 relative to the proximal support member. Therefore, the first trigger mechanism 250 may be operated to axially move the sleeve 340 to selectively cover and uncover the distal region 28 of the first body 20 of the endoprosthesis 10.

The first and second trigger mechanisms 250, 252 are configured for movement along and relative to the threaded rod 216 (FIGS. 4 and 5). The first and second trigger mechanisms 250, 252 may have any appropriate shape conducive to easy handling, such as, for example, rotating buttons in threaded engagement with the threaded rod 216. The first trigger mechanism 250 initially abuts the rear handle 222 and the second trigger mechanism 252 initially abuts the proximal end 212 of the delivery system. A series of snap-in locks 253 may be provided that snap onto the threaded rod 216 to prevent axial movement of the trigger mechanisms 250, 252 relative to the threaded rod until operation of the delivery system 200 is desired.

The outer sleeve 240 is co-axial with and extends over the tubes 300, 310, 320, and inner sleeve 340. The locking mechanism 230 is threadably engaged with the threaded rod 216 and connected to the outer sleeve 240 such that axial movement of the locking mechanism along the threaded rod causes corresponding axial movement of the outer sleeve relative to the rest of the delivery system 200. Another snap-in lock 253 may be provided that snaps onto the threaded rod 216 to prevent axial movement of the locking mechanism 230 relative to the threaded rod until operation of the delivery system 200 is desired.

The locking mechanism 230 may be configured such that rotation of the locking mechanism relative to the delivery system 200 causes minute or fine adjustment of the axial position of the outer sleeve 240 relative to the threaded rod 216 while strictly axial movement of the locking mechanism relative to the delivery system causes significant or course adjustment of the axial position of the outer sleeve. One such example of a locking mechanism 230 that may be used in accordance with the invention is taught in U.S. patent application Ser. No. 12/565,421, which is incorporated herein by reference in its entirety.

The delivery system 200 according to the present invention has a simple positioning and release procedure for the first and second bodies 20, 70 used to form the endoprosthesis 10 while allowing for necessary correction and fine adjustment in the case of inaccurate positioning. In other words, the delivery system 200 allows complete control on the part of the surgeon when implanting each body 20 and 70 of the endoprosthesis 10 in a manner as to afford extreme precision. In operation, the free ends 34, 52 of the proximal and distal regions 24, 28 of the first body 20 are crimped to the distal support member 242 and the proximal support member 244, respectively, in the manner described (see FIGS. 8A and 8B).

The second trigger mechanism 252 is then rotated in a single direction, e.g., clockwise, relative to the threaded rod 216 to cause the second trigger mechanism to move in the axial direction indicated generally by arrow A in FIG. 5 until the second trigger mechanism abuts the proximal end 212 of the delivery system 200. When the second trigger mechanism 252 moves in the axial direction A, the tube 300 secured thereto likewise moves in the direction A, causing the inner sleeve 330 to move axially in the direction A (FIG. 9A) and begin covering the distal support member 242 until the inner sleeve abuts distal edges of the projections 268 of the distal support member. In this configuration, the inner sleeve 330 overlies and covers the attachment members 39 of the proximal region 24 of the first body 20 to retain the proximal region of the first body in the openings 366 and passages 267, 270 of the distal support member 242.

Similarly, the first trigger mechanism 250 is then rotated in a single direction, e.g., counterclockwise, relative to the threaded rod 216 to cause the first trigger mechanism to move in the axial direction indicated generally by arrow B in FIG. 5 until the first trigger mechanism abuts the rear handle 222 of the delivery system 200. As the first trigger mechanism 250 moves in the axial direction B, the tube 320 secured thereto likewise moves in the direction B, causing the inner sleeve 340 to move in the direction B (FIG. 9B) and begin covering the distal support member 244. When the first trigger mechanism 250 abuts the rear handle 222, the inner sleeve 340 overlies and covers the attachment members 53 of the distal region 28 of the first body 20 to retain the distal region of the first body in the openings 286 and passages 287 of the proximal support member 244.

The locking mechanism 230 is then rotated and/or axially moved along the threaded rod 216 in the same direction B as the first trigger mechanism 250 to position the outer sleeve 240 entirely over the mounted first body 20 as shown in FIG. 4, i.e., covering both the proximal and distal support members 242, 244 to retain the first body in the compressed, covered condition.

Once the delivery system 200 loaded with the first body 20 of the endoprosthesis 10 is correctly positioned inside the artery, e.g., the abdominal aorta, the surgeon starts the release procedure of the first body from the delivery system. While holding the front handle 220 with one of his hands, the locking mechanism 230 is moved in the direction A (FIG. 10) by rotating and/or axially sliding the locking mechanism along the threaded rod 216. The locking mechanism 230 is moved in the direction A until the locking mechanism abuts the rear handle 222 (FIG. 11). This operation moves the outer sleeve 240 out of alignment with the first body 20 to expose portions of the proximal and distal support members 242, 244 as well as the intermediate 26 portion of the first body extending between the support members (not shown).

Although the first body 20 is partially exposed at this stage, the free end 34 of the proximal region 24 of the front body remains connected to the distal support member 242 and the free end 52 of the distal region 28 of the first body remains connected to the proximal support member 244 because the sleeves 330 and 340, respectively, still cover the openings 366 and 386 in the support members in which the attachment members 39, 53 are held. This allows the surgeon to still correct inaccurate positioning of the first body 20 within the vessel by moving the entire delivery system 200 backward or forward. For example, the connection between the free ends 34, 52 of the first body 20 of the endoprosthesis 10 and the distal support member 242 and proximal support member 244, respectively, allows for any necessary correction in the case of inaccurate positioning during the release of the first body or during the critical stages of the surgical procedures.

Figure 12:
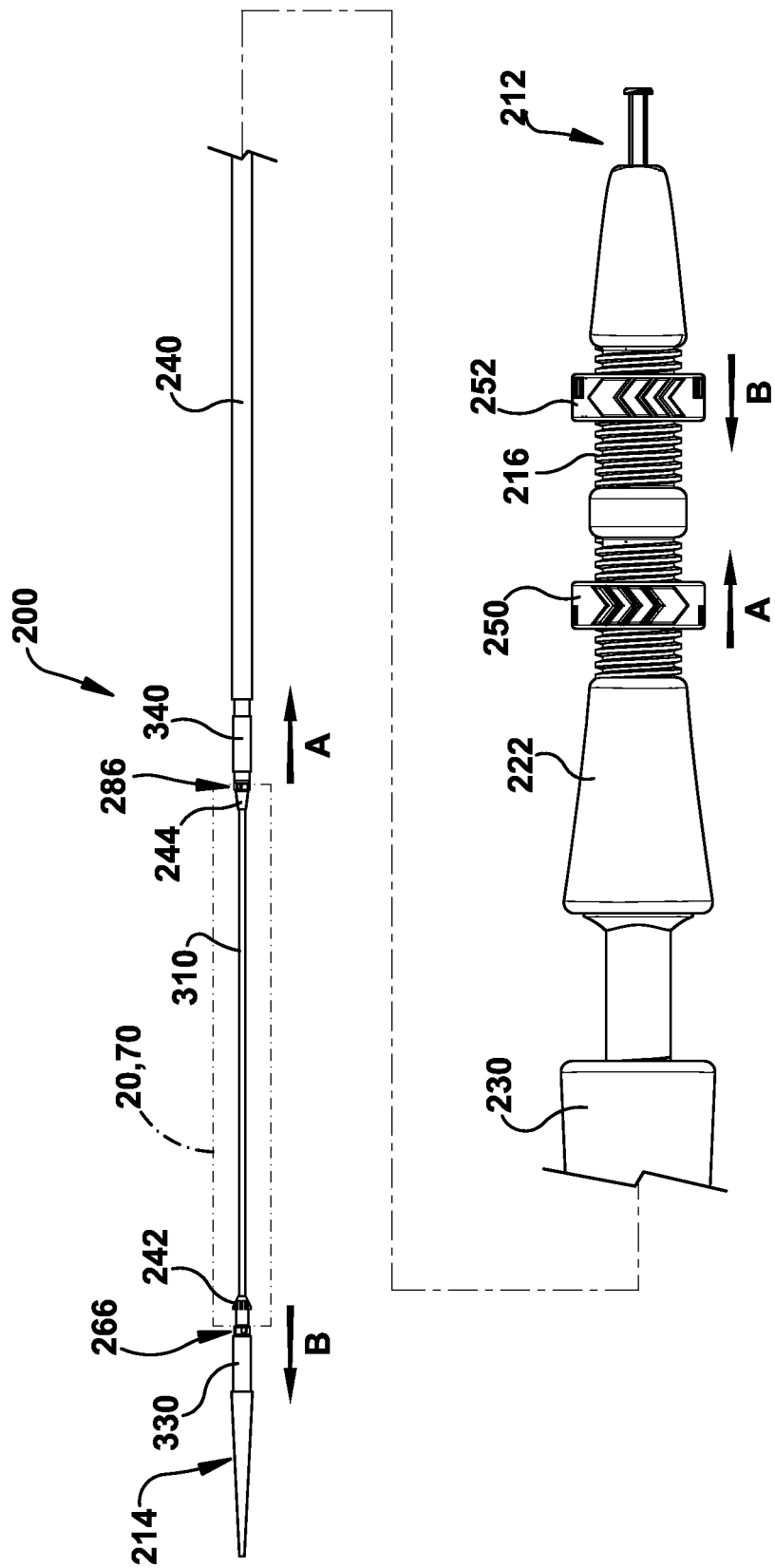
FIG. 12 illustrates the step of releasing ends of the first body of FIG. 1 from the delivery system of FIG. 4.

As shown in FIG. 12, when the correct position for the first body 20 of the endoprosthesis 10 has been established, the surgeon starts the procedure for releasing the free end 34 of the proximal region 24 of the first body 20 from the distal support member 242 in the following manner: while holding the rear handle 222 with one of his hands, the second trigger mechanism 252 is rotated relative to the threaded rod 216 in a single direction, e.g., counterclockwise, to move the second trigger mechanism in the direction B. This operation likewise moves the tube 300 secured thereto in the direction B and thereby moves the inner sleeve 330 in the direction B out of alignment with the openings 266 in the distal support member 242, which exposes the entire proximal region 24 of the first body 20 (not shown). The free end 34 of the proximal region 24 of the first body 20 is thereby allowed to self-expand to be released in the artery, which only leaves the free end 52 of the distal portion 28 of the first body connected to the delivery system 200 via the proximal support member 244. Once the free end 34 of the proximal region 24 of the first body 20 has been released, the surgeon may still correct any incorrect positioning of the first body by fine adjustment—but only by moving the entire delivery system 200 forward.

When the delivery system 200 is finally correctly positioned, the surgeon starts the procedure for releasing the free end 52 of the distal region 28 of the first body 20 of the endoprosthesis 10 from the proximal support member 244 by holding the rear handle 222 with one of his hands while rotating the first trigger mechanism 250 relative to the threaded rod 216 in a single direction, e.g., clockwise, with the other hand to move the first trigger mechanism in the direction A. This operation likewise moves the tube 320 secured thereto in the direction A and thereby moves the inner sleeve 340 in the direction A out of alignment with the openings 286 in the proximal support member 244, which exposes the entire distal region 28 of the first body 20 (not shown). The free end 52 of the distal region 28 of the first body 20 is thereby allowed to self-expand to be released in the artery. The first body 20 is now entirely released inside the artery and completely disconnected from the delivery system 200. The delivery system 200 for the endoprosthesis 10 may be retrieved from the patient by simply withdrawing it.

In summary, the procedure for using the delivery system 200 to implant the first body 20 of the endoprosthesis 10 may be performed according to the following stages:

In FIGS. 8A-8B, the free ends 34, 52 of the first body 20 are crimped onto the distal support member 242 and the proximal support member 244, respectively, and the sleeves 330, 340, and 240 are axially moved to completely cover the first body.

Figure 10:
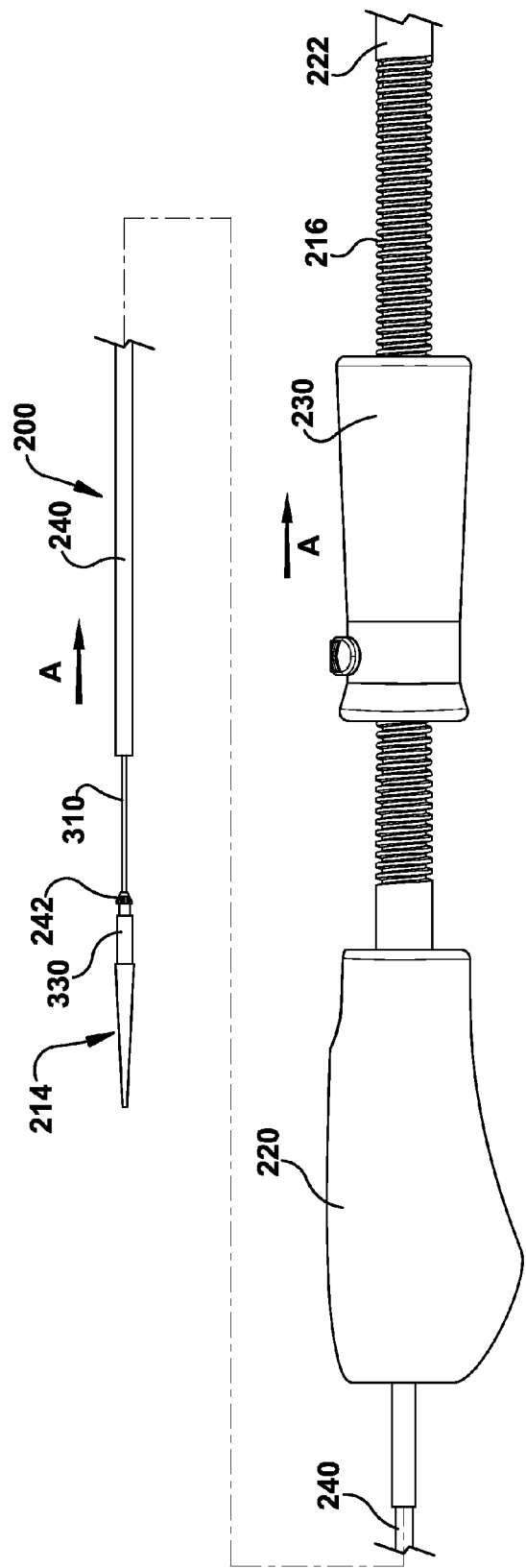
FIGS. 10-11 illustrate the step of exposing a portion of the first body of FIG. 1 on the delivery system of FIG. 4.
Figure 11:
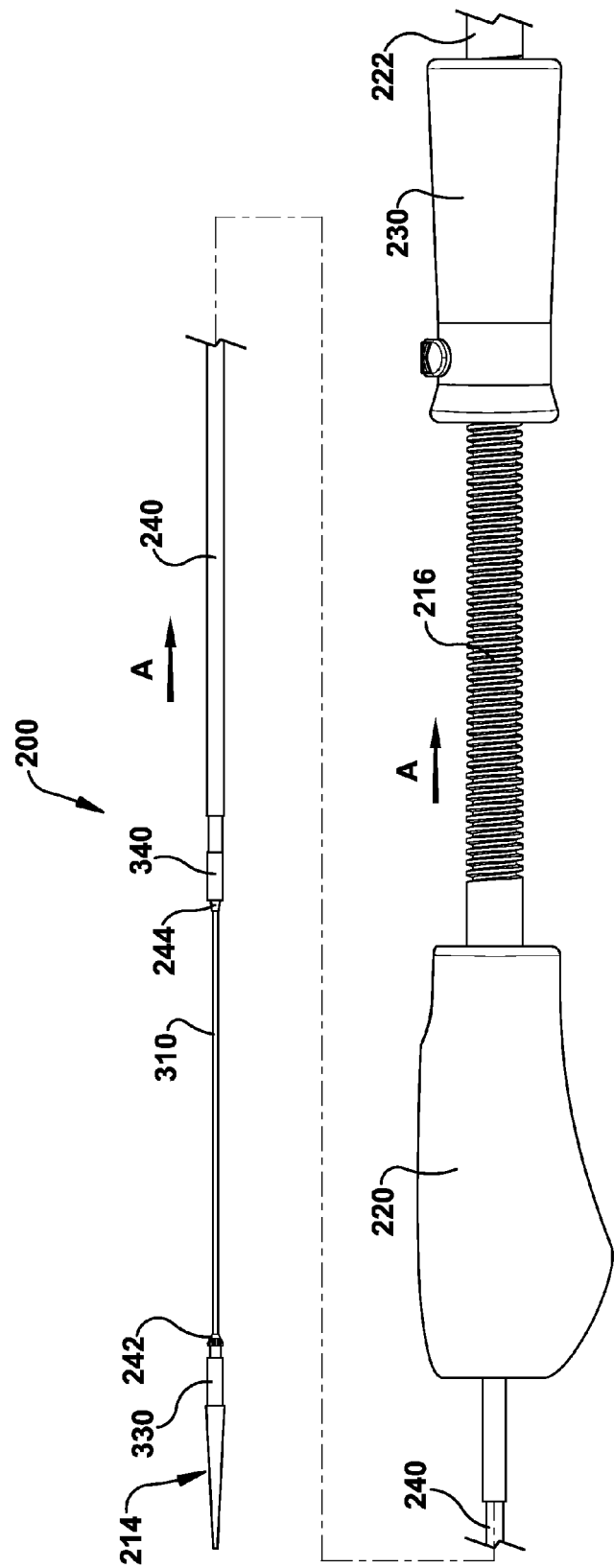

In FIGS. 10-11, the outer sleeve 240 is brought out of alignment with the first body 20 via the locking mechanism 230 to expose the intermediate region 26 of the first body 20 while the proximal and distal regions 24, 28 of the first body remain covered by the sleeves 330 and 340, respectively.

In FIG. 12, the free end 34 of the proximal region 24 of the first body 20 (or second body 70) is released from the distal support member 242 by moving the second trigger mechanism 252 in the direction B to push the sleeve 330 out of alignment with the distal support member via the first tube 300.

In FIG. 12, the free end 52 of the distal region 28 of the first body 20 is released from the proximal support member 244 by moving the first trigger mechanism 250 in the direction A to pull the sleeve 340 out of alignment with the proximal support member via the third tube 320. This allows the first body 20 (or second body 70) to self-expand and be implanted within the vascular site of the patient, such as shown schematically at 20, 70 in the example of FIG. 12.

As noted, the first body 20 and the second body 70 are pre-loaded onto two separate delivery systems 200. In other words, the second body 70 has its own delivery system 200 sized for its length but the loading and release of the second body into the vessel is identical to that of the first body 20. More specifically, the attachment members 88 on the proximal region 74 of the second body 70 are crimped into the openings 266 and passages 267, 270 in the distal support member 242 of the second delivery system 200 and held therein by axially moving the inner sleeve 330 into covering alignment with the openings via the second trigger mechanism 252 in the manner described. The attachment members 113 on the distal region 78 of the second body are crimped into the openings 286 and passages 287 in the proximal support member 244 and held therein by axially moving the inner sleeve 340 into covering alignment with the openings via the first trigger mechanism 250 in the manner described.

Once the outer sleeve 240 fully covers the second body 70 and following implantation of the first body 20 and removal of the first delivery system 200 from the vessel, the second delivery system 200 positions the second body within the vessel in the same manner as the first body 20 and, using the same steps described above, releases the second body from the second delivery system into the first body 20 already implanted within vascular site to form the assembled endoprosthesis 10. The delivery system 200 of the present invention therefore implants the endoprosthesis 10 in a piecewise manner into the vascular site with precision and repeatability.

All patent applications and publications mentioned in the above description are indicative of the level of expertise of those skilled in the art relating to the invention. All the patent applications and publications are included herein as reference in the same extent that each individual patent application or publication was specifically indicated to be indicated as reference.

What have been described above are examples. It is, of course, not possible to describe every conceivable combination of components or methods, but one of ordinary skill in the art will recognize that many further combinations and permutations are possible. Accordingly, the invention is intended to embrace all such alterations, modifications, and variations that fall within the scope of this application, including the appended claims. Additionally, where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, the term "including" means including but not limited to. The term "based on" means based at least in part on.

Having described the invention, the following is claimed:

1. An endoprosthesis delivery system for implantation of an endoprosthesis at a bifurcation between a main vessel and at least two secondary vessels comprising:
    an endoprosthesis, comprising:
        first and second bodies, each comprising:
            a self-expanding and flexible structure,
            the flexible structure including a proximal region, an intermediate region, and a distal region, the distal region terminating at a free end, and
            the flexible structure defining a leg and an endoprosthesis support member, the endoprosthesis support member being adjacent to and spaced apart entirely from the leg, the leg terminating at the free end of the distal region,
        the second body being configured for positioning within the first body,
        the proximal region of the first body including a free end configured for positioning within the main vessel, the leg of the first body being configured for positioning within a first secondary vessel, the leg of the second body being configured for positioning within a second secondary vessel; and
    a delivery system, comprising:
        a catheter including a proximal end and a distal end, the distal end being adapted for insertion into a vessel, the first body being positioned within the distal end of the catheter in a reduced cross-sectional condition;
        a first tube, a second tube, and a third tube extending from the proximal end towards the distal end of the catheter;
        a first support member and a second support member connected to the first tube, the free end of the proximal region of the first body being releasably connected to the first support member and the free end of the distal region of the first body being releasably connected to the second support member;
        an outer sleeve movable along the catheter from a first position overlying the endoprosthesis to a second position spaced from the first body;
        a first inner sleeve connected to the second tube for selectively covering the free end of the proximal region of the first body;
        a first trigger mechanism coupled to the second tube for releasing the free end of the proximal region of the first body of the endoprosthesis from the first support member;
        a second inner sleeve connected to the third tube for selectively covering the free end of the distal region of the first body; and
        a second trigger mechanism coupled to the third tube to pull the second inner sleeve away from the second support member for releasing the free end of the distal region of the first body from the second support member, the first and second trigger mechanisms being movable in different directions along the catheter to release the free ends of the proximal and distal regions of the first body from the first and second support members; and
    wherein the first trigger mechanism is configured to be rotated relative to the catheter to push the first inner sleeve away from the first support member to release the free end of the proximal region of the first body from the first support member.

2. The endoprosthesis delivery system recited in claim 1, wherein the second body is configured to be positioned within the first body such that the proximal region of the second body is positioned within the proximal portion of the first body, the leg of the second body extending through the endoprosthesis support member of the first body, the endoprosthesis support member of the second body extending into the leg of the first body.

3. The endoprosthesis delivery system recited in claim 2, wherein when the second body is configured to be positioned within the first body such that the free end of the proximal region of the first body is configured for attachment to a wall of the main vessel, with the proximal region of the second body cooperating with the proximal region of the first body to increase outward support within the wall of the main vessel, the leg of the first body being configured for attachment to a wall of the first secondary vessel, the leg of the second body being configured for attachment to a wall of the second secondary vessel.

4. The endoprosthesis delivery system recited in claim 1, wherein the flexible structure that forms the proximal region and the intermediate region of the first body are separate and axially spaced apart from each other to provide an unsupported portion there between in the first body, the flexible structure of the proximal region of the second body being configured to axially align with the unsupported portion of the first body when the second body is inserted in the first body.

5. The endoprosthesis delivery system recited in claim 1, wherein the proximal region of the second body includes at least one attachment member for securing the proximal region of the second body to the proximal region of the first body.

6. The endoprosthesis delivery system recited in claim 1, further comprising a lining attached to the intermediate regions of each of the first and second bodies, the free end of the proximal region of the first body and the free end of the distal region of each of the first and second bodies being free of the lining.

7. The endoprosthesis delivery system recited in claim 6, wherein the proximal region of the second body includes at least one attachment member for securing the proximal region of the second body to the proximal region of the first body.

8. The endoprosthesis delivery system recited in claim 6, wherein a portion of the lining on the first body between the proximal region and the intermediate region is unsupported by the flexible structure of the first body, the second body including a reinforcing member that is axially aligned with the unsupported portion of the lining for reinforcing the unsupported portion of the lining when the second body is positioned within the first body.

9. The endoprosthesis delivery system recited in claim 1, wherein the free end of the proximal region of the first body is larger in axial cross-section than the free end of the distal region of the first body.

10. The endoprosthesis delivery system recited in claim 1, the delivery system further comprising a locking mechanism connected to the outer sleeve and configured to move the outer sleeve from the first position to the second position.

11. The endoprosthesis delivery system recited in claim 1, the delivery system further comprising a threaded rod through which the first inner sleeve and the second inner sleeve extend, the first trigger mechanism being rotatable about the threaded rod to push the first inner sleeve away from the first support member to release the proximal region of the first body from the first support member, the second trigger mechanism being rotatable about the threaded rod to pull the second inner sleeve away from the second support member to release the distal region of the first body from the second support member.

12. An endoprosthesis delivery system for implantation of an endoprosthesis at a bifurcation between a main vessel and at least two secondary vessels comprising:
an endoprosthesis, comprising:
a first body, comprising:
a self-expanding and flexible structure, the flexible structure including a proximal region, an intermediate region, and a distal region, the proximal region terminating at a first free end;
a lining connected with and extending along the proximal region, the intermediate region, and the distal region of the flexible structure, the first free end of the flexible structure being free of the lining, the distal region terminating at a second free end that is free of the lining, the second free end including one or more attachment loops,
the flexible structure not extending along the entire length of the lining, and
the flexible structure being configured to define a leg and an endoprosthesis support member adjacent to the leg, the leg terminating at the second free end of the distal region, the leg configured for positioning within a first secondary vessel,
a second body, comprising:
a self-expanding and flexible structure, the flexible structure of the second body including a proximal region, an intermediate region, and a distal region, the proximal region terminating at a third free end;
a lining connected with and extending along the proximal region, the intermediate region, and the distal region of the flexible structure, the third free end of the flexible structure being free of the lining, the distal region terminating at a fourth free end that is free of the lining, and
the flexible structure configured to define a leg and an endoprosthesis support member to the leg, the leg terminating at the fourth free end of the distal region,
the second body being configured to be positioned within the first body such that the proximal region of the second body is positioned within the proximal region of the first body, the leg of the second body extending through the endoprosthesis support member of the first body and the endoprosthesis support member of the second body being aligned with and opening into the leg of the first body; and
a delivery system, comprising:
a catheter including a proximal end and a distal end, the distal end being adapted for insertion into a vessel, the first body being positioned within the distal end of the catheter in a reduced cross-sectional condition;
a first tube, a second tube, and a third tube extending from the proximal end towards the distal end of the catheter;
a first support member and a second support member connected to the first tube, the free end of the proximal region of the first body being releasably connected to the first support member, the attachment loops at the free end of the distal region of the first body being releasably received in corresponding openings in the second support member;
an outer sleeve movable along the catheter from a first position overlying the endoprosthesis to a second position spaced from the first body;
a first inner sleeve connected to the third tube for selectively covering the attachment loops at the free end of the distal region of the first body;
a first trigger mechanism coupled to the third tube for releasing the free end of the distal region of the first body of the endoprosthesis from the second support member;
wherein the first trigger mechanism is configured to be rotated relative to the catheter to pull the first inner sleeve away from the second support member to release the free end of the distal region of the first body from the second support member;
a second inner sleeve connected to the second tube for selectively covering the free end of the proximal region of the first body;
a second trigger mechanism coupled to the second inner sleeve for releasing the free end of the proximal region of the first body from the first support member; and
a threaded rod through which the first inner sleeve and the second inner sleeve extend, the first trigger mechanism being rotatable about the threaded rod to pull the first inner sleeve away from the second support member to release the distal region of the first body from the second support member, the second trigger mechanism being rotatable about the threaded rod to push the second inner sleeve away from the first support member to release the proximal region of the first body from the first support member.

13. The endoprosthesis delivery system recited in claim 12, wherein a portion of the lining on the first body between the proximal region and the intermediate region is unsupported by the flexible structure of the first body, the second body including a reinforcing member of the flexible structure that is configured for axial alignment with the unsupported portion of the lining of the first body for reinforcing the unsupported portion of the lining.

14. The endoprosthesis delivery system recited in claim 12, the delivery system further comprising a snap-in lock for releasably engaging the catheter to prevent movement of the first and second trigger mechanisms.

* * * * *